United States Patent [19]
della Valle et al.

[11] Patent Number: 5,506,224
[45] Date of Patent: Apr. 9, 1996

[54] N-ACYL DERIVATIVES OF AMINOALCOHOLS ACTIVE AS LOCAL AUTACOIDS AND USEFUL IN THE THERAPY OF AUTOIMMUNE PROCESSES

[75] Inventors: Francesco della Valle; Silvana Lorenzi, both of Padova; Jacobus C. J. J. Samson, Selvazzano Dentro; Federica della Valle, Padova, all of Italy

[73] Assignee: Lifegroup S.P.A., Rome, Italy

[21] Appl. No.: 148,557

[22] Filed: Nov. 8, 1993

Related U.S. Application Data

[63] Continuation-in-part of Ser. No. 998,688, Dec. 30, 1992, abandoned.

[30] Foreign Application Priority Data

Dec. 31, 1991 [IT] Italy ................... MI91A3508

[51] Int. Cl.$^6$ .......... A61K 31/16; A61K 31/38; A61K 31/455; A61K 31/575
[52] U.S. Cl. .......... 514/182; 514/354; 514/356; 514/440; 514/448; 514/563; 514/564; 514/567; 514/825; 514/863; 514/885; 514/886; 514/887; 514/903; 514/914
[58] Field of Search .................. 514/563, 903, 514/885, 182, 354, 356, 440, 448, 564, 567, 825, 863, 886, 887, 914

[56] References Cited

U.S. PATENT DOCUMENTS

| | | | |
|---|---|---|---|
| 3,387,008 | 6/1968 | Cawley et al. | 260/404 |
| 4,996,193 | 2/1991 | Hewitt et al. | 514/11 |

FOREIGN PATENT DOCUMENTS 2140369  1/1973  France .

OTHER PUBLICATIONS

Ganley et al. "Anti–inflammatory Activity of Compounds . . ." *J. Lab. & Clin. Med.* 51:709–714. 1958.

Perlik et al. "Anti–inflammatory Properties of N(2–Hydroxyethyl) Palmitamide". *Acta Physiologica Scientiarum Hungaricae*, 39:395–400. 1971.

F. Perlik et al, "Future Trends in Inflammation", 1974, Piccin Medical Books, Verona, London, Paris, p. 301, p. 305, paragraph 1.

IRCS Med. Sci., vol. 11, No. 10, 1983, pp. 899–900, Dennis E. Epps, "Protective effects of N–acylethanolamines, an endogenous class of lipid amides, on hypoxid guinea pig heart".

J. Allergy Clin. Immunol. vol. 86, No. 4(2), 1990, pp. 677–683, Joann M. Mican et al., "Arthritis and Mast Cell Activation".

Laboratory Investigation, vol. 48, No. 3, 1983, pp. 332–338, Henry C. Powell, "Early Changes in Experimental Allergic Neuritis".

Boll. Soc. Ital. Biol. Sper., vol. 44, No. 9, 1968, pp. 809–813, F. Benvenuti et al, "Attivita di alcuni derivati della palmitoiletanolamide sull'edema da carragenina nella zampa di ratto" (English Abstract Provided).

Rheumatic Disease Clinics of North America, vol. 17, No. 2, 1991, pp. 333–342, Barry L. Gruber, "Immunoglobulin E, Mast Cells, Endogenous Antigens, and Arthritis".

Am. Rev. Resp. Dis., vol. 135, No. 6(2), 1987, pp. S5–S8, John Bienenstock et al, "Mast Cell Involvement in Various Inflammatory Processes".

Arch. Dermatol. Res., vol. 280, 1988, pp. 189–193, B. Toruniowa et al, "Mast Cells in the Initial Stages of Psoriasis".

(List continued on next page.)

*Primary Examiner*—S. Mark Clardy
*Attorney, Agent, or Firm*—Stevens, Davis, Miller & Mosher

[57] ABSTRACT

N-acyl-derivatives of hydroxyamines suitable for the therapeutic treatment of pathologies characterized by degranulation of mast cells caused by a neurogenic and/or immunogenic hyperstimulation.

25 Claims, 1 Drawing Sheet

OTHER PUBLICATIONS

Acta Neurol. Scand., vol. 81, 1990, pp. 31–36, Kruger et al., "Mast Cells and Multiple Sclerosis: a light and electron microscopic study of mast cells in multiple sclerosis emphasizing staining procedures".

Coburn et al, "A Limited Clinical Evaluation of an Egg Yolk Fraction in the Prevention of Rheumatic Recurrences", *Arch. Ineram. Rheumatolog*, vol. 3, No. 4, (1960), pp. 498–525.

Long et al, "Opposite Actions of Thyroid and Adrenal Hormones in Allergic Hypersensitivity", *Lance*, Mar. 18, (1950), pp. 492–495.

Ganley et al, "Antianaphylactic and Antiserotonin Activity of a Compound Obtained From Egg Yolk, Peanut Oil, and Soybean Lecithin", *Allergy*, 30, Sep.–Oct. (1959), pp. 415–419.

Kuehl et al, "The Identification of N–(2–Hydroxyethyl)–Palmitamide as a Naturally Occurring Anti∝Inflammatory Agent", *American Chemical Society*, 79, (19), (1957), pp. 5577–5578.

Somerharju et al., "Glycerophospho–(N–Acyl)–Ethanolamine Lipids in Degenerating BHK Cells", *Biochimica et Biophysica Acta*, 573, (1979), pp. 83–89.

Epps et al, "N–Acylethanolamine Accumulation in Infaracted Myocardium", *Biochemical and Biophysical Research Communications*, 90, (2), (1979), pp. 628–633.

Russian Publication, pp. 17–22. A. M. Karnauch et al 1961.

Colodzin et al, "Enzymatic Formation of Fatty Acid Amides of Ethanolamine", *Biochemical and Biophysical Research Communications*, vol. 10, No. 2, (1963), pp. 165–170.

Wren J. J. et al, "Precursors of N–Acylethanolamines in Hen's Egg–Yolk Lipid", *Biochimica et Biophysica Acta*, 98, (1965), pp. 589–597.

Bachur et al, "Microsomal Synthesis of Fatty Acid Amides", *The Journal of Biological Chemistry*, vol. 241, No. 6, Mar. 25, (1966), pp. 1308–1313.

Goth et al, "Tissue Thromboplastins and Histamine Release From Mast Cells", *Life Sciences*, No. 9, (1962), pp. 459–465.

Gray G. M., "Phosphatidyl–(N–Acyl)–Ethanolamine A Lipid Component of Mammalian Epidermis", *Biochimica et Biophysica Acta*, 431, (1976), pp. 1–8.

Publication "Suggestions and Instructions to Authors", vol. 90, pp. 1965–1966. 1967.

*Publications* "Concerning Synthetic Preparations and Therapeutical Uses of PEA and Long Chain Fat Acids Mono– and Di–Ethanolamides", (*Abstracts* 1–16), Part A. (Abstracts from multiple years).

*Patents* "Recording Synthetic Preparations PEA, Long Chain Fat Acids Mono– and Di–Ethanolamides", (*Abstracts* 18–19), Part B. 1968.

*Patents* "Relating to Therapeutical Uses of PEA, Long Chain Fat Acids Mono– and Di–Ethanolamides", (*Abstracts* 20–26), Part C. (multiple years).

*Patents* "Referring to Cosmetic Uses of PEA, Long Chain Fat Acids Mono– and Di–Ethanolamides", (*Abstracts* 27–39), Part D. (multiple years).

CA85(9):62689v (1976).

N-ACYL DERIVATIVES OF AMINOALCOHOLS ACTIVE AS LOCAL AUTACOIDS AND USEFUL IN THE THERAPY OF AUTOIMMUNE PROCESSES

This application is a continuation-in-part of application Ser. No. 07/998,688, filed Dec. 30, 1992, now abandoned.

FIELD OF THE INVENTION

The present invention relates to the use of N-acylderivative of hydroxyamines as the active ingredients for preparing pharmaceutical compositions for the treatment of autoimmune pathologies.

PRIOR ART

It is known that specific cells, the mast cells, normally acquiescent, can be activated by particular neurogenic and immunogenic stimuli and this activation results in mast cell degranulation, and subsequent to the release of substances which, on their own, produce prevailingly cytotoxic effects having a meaningful relevance in autoimmune pathologies.

Autoimmune pathologies are in fact characterized by autoaggression pathologic processes wherein the effector system is formed by immunocompetent cells and among them the mast cells result to be of meaningful importance.

The mast cells are in fact a cellular population residing in tissues and when stimulated determine mainly a localized tissue damage.

This is particularly important when considering that a pathologic process detrimental to individual and specific tissues (for example the nervous system in multiple sclerosis) is a general feature of autoimmune pathologies.

The autoaggressive potential of mast cells is substantially obtained (by releasing cytotoxic substances cytokins and in particular the Tumour Necrosis Factor=TNF), contained in the preformed granules inside the mast cells and rendered massively available by the degranulation process.

The mast cells activity is regulated by stimulating neuromediated and immunomediated systems showing an agonist action towards degranulation, and counterbalanced by antagonist and degranulation inhibitory systems, namely mechanisms intervening in general and in local circuits.

In fact since long a general circuit of antagonist control has been identified in corticosteroid hormones, which is activated by generalized stimulations and is able to act also on the mast cells.

The prior art encompasses that exogenous corticosteroids are used in different ways to approximately produce this antagonist effect in order to fight both local and systemic inflammatory phenomena. The chronical use of corticosteroids determines considerable side effects, such as the tissue atrophy (for example the cutaneous one in case of a dermatologic use), water retention (Cushing -like syndrome), or the most serious immunosuppression caused by imbalance of adrenal hypophysis axis.

The more these side effects are serious, the more the therapeutic use becomes concomitantly systemic and chronical.

It was actually supposed that close to the general system of inactivation phenomena connected to mast cell degranulation, an antagonist type control local system or a complex of such local systems exists, which the same cell is able to locally activate in case of hyperstimulation, resorting to endogenous substances able to act as autacoids (agonist action—antagonist reaction system connected with mast cells and their degranulation).

It is furthermore known that N- palmitoylethanolamide was tested in order to verify the possible therapeutic effects, and it was ascertained that it shows a generic activity in inhibiting the inflammatory response of the tested animal, but this effect was not significant when the same substance, extracted from yolk egg, was administered to man with therapeutic purposes. (Coburn et al, Arch. Interam. Rheumatolog. 1960, 4, 498–515).

It is in fact known from the early fifties the quite casual discovery of an antiinflammatory activity of a lipidic excipient utilized as the vehicle in an antirheumatic drug (Long D. A. and Miles A. A. Lancet 1950, p. 492).

The successive research directed to find this agent showing such an activity, evidenced its presence both in vegetable material (peanuts oil, soya seeds) and in animals (mainly in yolk egg) (Oswald H. et al., J: Allergy, 1959, 30, 415–419).

Only in the second half of the fifties, Kuehl et al (J. American Chemical Society, 1957, 79 (19) pp 5577/8 could isolate this substance and define its chemical structure, which was confirmed to be of N-palmitoyl-ethanolamide (N-PEA), also on the base of comparisons with same product obtained by chemical synthesis (Ganley O. H. et al., J. Lab. and Clin. Med., 1958, 51 (5), pp709–714).

An intense research activity directed to characterize the pharmacological profile of this substance and its therapeutical potential, followed the above experimental evidences, and it was carried out by Czechoslovak researchers.

Then it was found that this product is also able to increase the animals resistance to different bacterial toxins and experimental infections.

And it is on the base of this assumption that in the early seventies a pharmaceutical composition containing N-PEA as the active ingredient was launched in Czekoslovakia, whose therapeutical indication was the prevention of the respiratory tract infections but it actually had a poor luck, and was then retired from the market.

Notwithstanding the poor interest in pharmaceutical applications, the research on this class of endogenous compounds continued for a long period.

The identification of these compounds in germinal cellular layers or in specific differentiation and/or degeneration states (Gray G. M., Biochem., Biophys. Acta,1979,573, p.83–89) induced to hypothize the existence of a specialized functional role for these compounds, although it was initially hypothized that these compounds were the results of catabolic pathway activations and therefore were degradation products.

The possibility that these compounds could represent a physiologic form of defence, directed to block and/or reduce the damage induced by hypotoxic stress, was clearly put forth by Epps et al. (Biochem, Biophys, Res. Comm., 1979, 90 (2), p.628–633), who found high concentrations of N-acylethanolamine in myocardium areas affected with infarction in the dog after coronaric ligature.

It was supposed by these authors that the above products had a particular meaning with reference to the antiinflammatory activity of N-PEA previously found, without, however, indicating a possible mechanism and/or a preferential site which could correlate the two experimental observations, namely its accumulation in hypotoxic areas, and its antiinflammatory activity.

SUMMARY OF THE INVENTION

The Assignee has now found that mast cells degranulation may be effectively antagonized by administering N-acyl derivatives of hydroxyamines.

Therefore the present invention relates to the use of these N-acyl derivatives for the preparation of pharmaceutical compositions suitable for the treatment of both human and animal pathologies, characterized by mast cells degranulation consequent to a neurogenic and/or immunogenic hyperstimulation.

These N-acylderivatives act as local autacoids and are particularly suitable in the therapy of autoimmune processes.

DETAILED DESCRIPTION OF THE INVENTION

Figure 1:
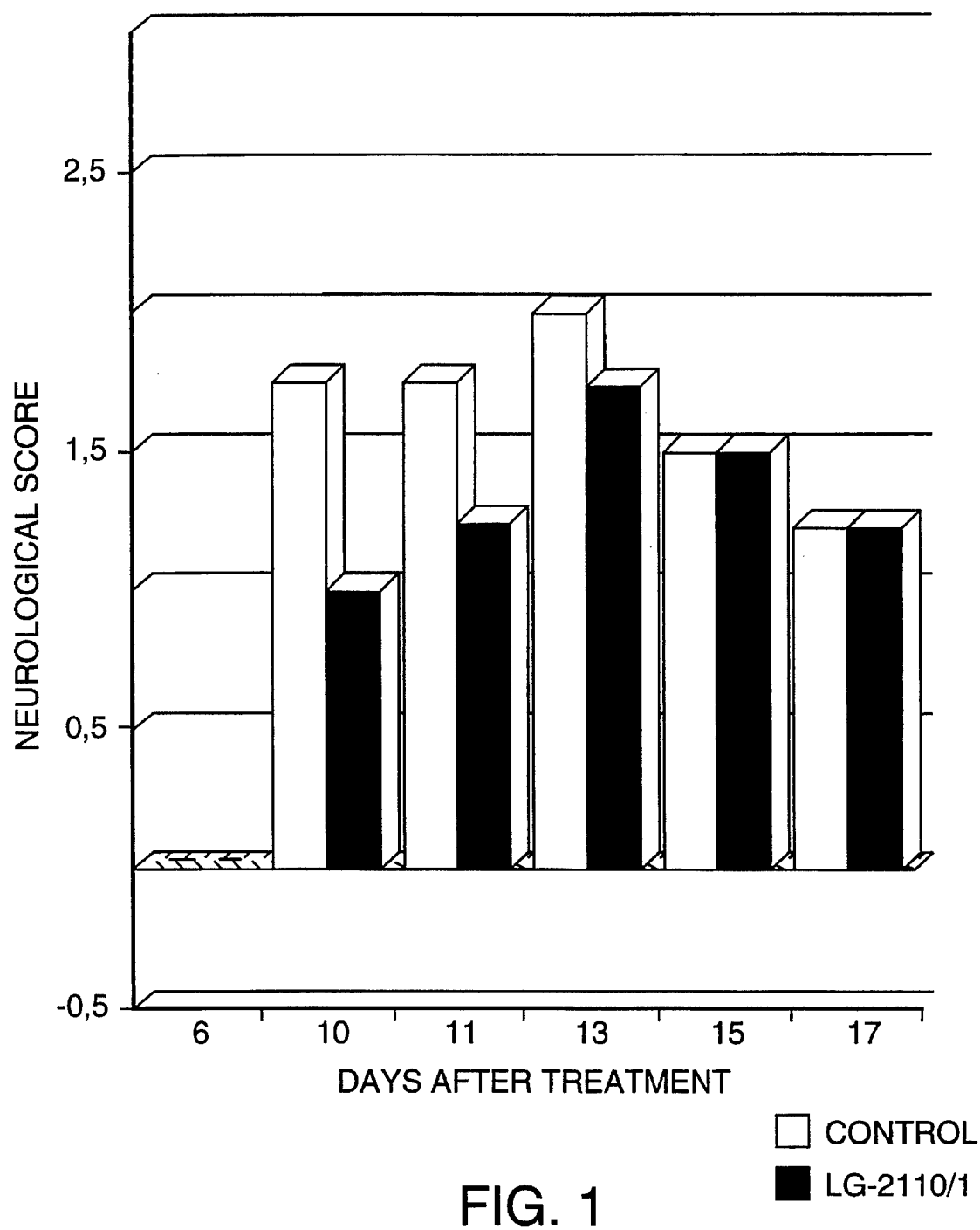
FIG. 1 represents the effect of palmitoylethanolamide (LG2110/1) oral treatment on experimental allergic encephalomyelitis (encephalitis) induced by 1–9 NacMBP.

The features and advantages of the N-acyl derivatives acting as local autacoids and useful in the treatment of pathologies characterized by mast cells degranulation, according to the present invention, will be better understood in the course of the present detailed description.

The assignee has surprisingly found that the activity of a broad class of N-acyl derivatives does not limit to a generic and modest antiinflammatory activity as suggested by the prior art relating to PEA, but that this activity plays an important role in the local inhibition of mast cell degranulation.

This allows to utilize the substances belonging to said class, in pharmaceutical formulations having not only antiinflammatory activity, but also being able to modulate mast cell degranulation and therefore to inhibit the undesired effects of autoimmune processes.

In other words it was identified a specific class of pharmaceutically active substances suitable to locally perform by exogenous route an antagonist function of the damaging autoimmune processes, and therefore suitable to show therapeutical effects in these processes both in human and animals.

Some substances, at the level of the actual knowledge, were found inside this class to be more suitable, than other ones to show this activity, which however is claimed for the whole class.

In order to define better the present invention the compounds capable to modulate the mast cell degranulation belong to the class of the N-acyl derivatives of general formula:

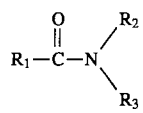

wherein $R_2$ is a residue selected from a $C_1$-$C_{20}$ linear or branched alkylene-hydroxy, optionally susbstituted in the alkylene chain with at least one aryl group of from 6 to 20 carbon atoms, and a hydroxyarylene of from 6 to 20 carbon atoms optionally substituted in the aromatic ring with at least one alkyl group of from 1 to 20 carbon atoms, and $R_3$ is H or it is=$R_2$; whereas $R_1CO$- is an acyl radical of a monocarboxylic acid belonging to one of the following classes:

a) a linear or branched aliphatic acid of from 2 to 20 carbon atoms, optionally containing at least one ethylenic unsaturation;

b) a linear or branched aliphatic acid of from 1 to 20 carbon atoms; optionally having at least one ethylenic unsaturation, and always having from one to two substituents selected from the group consisting of: OH; $NH_2$; $R_4$—CO, wherein $R_4$ is a $C_1$-$C_{10}$ alkyl; an aryl group of from 6 to 20 carbon atoms, a heterocycyclic group consisting of a ring of from 5 to 6 atoms and containing as the heteroatoms from 1 to 2 N or S atoms; a cycloalkenyl group of from 5 to 6 carbon atoms containing at least one $C_1$-$C_{10}$ alkyl group;

c) is an aromatic acid of from 6 to 20 carbon atoms, optionally substituted in the aromatic ring with at least one substituent selected from the group consisting of: hydroxy, $NH_2$, $OCOR_4$, $OR_4$, wherein $R_4$ has the above mentioned meanings, $SO_3H$;

d) an aromatic heterocyclic monocarboxylic acid, whose ring consists of from 5 to 6 atoms containing as the heteroatoms from 1 to 2N or S atoms;

e) a biliar acid.

Preferred residue $R_3$ and/or $R_2$ according to the present invention, for a merely illustrative but not limitative purpose, are those of monoethanolamine, diethanolamine, 2-hydroxy-propylamine, di-(2-hydroxypropylamine), which bring to the compounds having the following formulas:

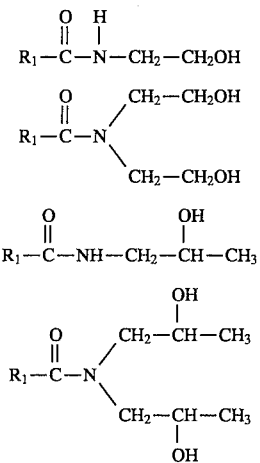

The N-acyl derivatives of (2-idroxy)-propylamine and of di-(2-hydroxypropylamine) may be an optically active isomer or a racemate.

For merely illustrative purposes, when $R_1CO$- is an acyl radical of a monocarboxylic acid belonging to class (a) it is preferably selected from the group consisting of: palmitic acid, stearic acid, pentadecanoic acid, eptadecanoic acid, lauric acid, myristic acid, acetic acid, butirric acid, linoleic acid, valeric acid, caprylic acid, valproic acid, oleic acid, undecenoic acid, arachidonic acid.

In particular when $R_1CO$- is an acyl radical of a monocarboxylic acid belonging to class (b) it is preferably selected from the group consisting of: gamma-hydroxybutirric acid, gamma-amino butyric acid, lactic acid, α-lipoic acid, retinoic acid, phenyl-hydroxy-acetic acid, pyruvic acid, glycolic acid.

When $R_1CO$- is an acyl radical of a monocarboxylic acid belonging to class (c) it is preferably selected from the class consisting of: salicylic, acetylsalicylic, sulfosalicylic, benzoic, p-amino benzoic, trimethoxybenzoic, phenylanthranylic acid.

In the case $R_1CO$- is an acyl radical of a monocarboxylic acid belonging to class (d) it is is preferably selected from the group consisting of nicotinic acid, isonicotinic acid, thenoic acid, when it is an acyl radical of a monocarboxylic acid belonging to class (e) it is preferably deoxycholic acid.

The whole class of the above substances and referring in particular to the N-acyl derivatives of ethanolamine and diethanolamine, (2-hydroxypropyl)-amine and di-(2-hydroxypropyl)amine can be advantageously used in all the pathologies having prevailingly autoimmune origin, wherein it is necessary to locally and selectively modulate the mast cell activity.

This modulation accomplished by controlled inhibition of the degranulation process of the mast cell activated by neuroimmunogenic stimulations, acting by pharmacological route with the substances of the present invention, results to be an important therapeutical instrument in all the pathologies in human beings and animals in which the mast cell represents the ethiopathogenetic effector, and therefore in all the pathologies wherein a massive or chronic mast cell activation plays an important pathogenetic role, in particular in multiple sclerosis and psoriasis.

In fact in multiple sclerosis the pathologically activated mast cells seem to be essential for the plaques development in CNS, for compromising the hematoencephalic barrier, for the adhesion of the infiltrating mast cells from the vasal compartment and finally for the release of the aggressive cytokin the Tumour Necrosis Factor, which is on its turn the final aggressor of the myelinic structures and the final cause of the histic damages (Toms R. et al., J. Neuroimmunology, 1990, 30, pp 169–177; Kruger P. G. et al., Acta Neurol. Scand., 1990, 81, pp 31–36).

Also in psoriasis the chronic localized inflammation seems to be directly correlated to a defective mast cells activation.

As a matter of fact the mast cell degranulation intervenes precociously during the development of the psoriasis lesions, whereas under chronic conditions a considerable increase is observed in the number of mast cells present in the lesions. (Toyry S. et al., Arch. Dermatol. Res., 1988, 280, pp-282-285; Toruniowa B. and Jablonska S., Arch. Dermatol. Res., (1988, 280, pp 189–193).

These two pathologies are not to be considered as a limitative example of the possible application of the compounds according to the present invention, since they are not the only ones wherein the mast cells activation is to be considered the precocious etiopathogenetic moment of the autoaggresive processes.

All the compounds of the present invention may find an advantageous therapeutic application depending on their specific activity in the treatment of dermatologic pathologies having immune origin, such as atopic dermatitis, dermatomyositis, scleroderma, polymyositis, pemphigus, pemphigoid, epidermolysis bullosa, or of ophtalmic pathologies such as Sjogren's syndrome, sympathetic ophtalmia, autoimmune uveitis and uveoretinites, or again in articular and connective pathologies, such as rheumatic arthritis, psoriatic arthritis, systemic lupus erythematosus arthritis, systemic or discoide lupus erythematosus.

Other pathologic conditions, in which it is therapeutically useful the local control of the mast cells degranulation process are the chronic inflammatory pathologies, having autoimmune origin, as for example the chronic inflammations of the gastrointestinal mucous membranes (Crohn's disease). Furthermore, with regard to the animal pathology, the above described effect exerted by these new derivatives, is useful in the therapy of ophtalmic pathologies, i.e. Sjogren's Syndrome and Keratoconjunctivitis sicca; in articular and connective phatologies and moreover grastointestinal inflammation having autoimmune origin.

As regards the present invention innovation of the pharmacologic approach, which is directed to intervene onto a single site of action by means of the modulation of a local endogenous autodefence system, experimentation was carried out in order to verify if N- PEA might perform the role of a local autacoid, specifically aimed to the mast cells acting as an effector system involved by the nervous system, the immune system and the endocrinous system, also in the case this product is administered by exogenous route.

It was further demonstrated that other compounds of the present invention show the same type of pharmacological activity.

We report herewith the following examples of preparation of the N-acyl derivatives according to the present invention for illustrative but not limitative purposes.

EXAMPLE 1- SYNTHESIS OF N-PALMITOYLETHANOLAMIDE (N-PEA)

Following Roe et al's instructions (J. Am. Chem. Soc., 1952, 74, 3442–3443), the N-palmitoylethanolamide synthesis was accomplished by reacting under reflux ethanolamine and palmitic acid.

Particularly 1 mole of palmitic acid is reacted with 1.5 moles of ethanolamine in ethyl ether for 5–6 hours under nitrogen atmosphere.

The reaction product is then extracted from the reaction mixture and crystallized by using 95% ethanol at 0° C. N-PEA melting point is about 94°–95° C.

The physicochemical properties of N-PEA, obtained according to the present example are reported hereinbelow.

| | |
|---|---|
| physical state | crystalline powder |
| raw formula | $C_{18}H_{37}NO_2$ |
| molecular weight | 299.48 |
| elemental analysis | C = 72.19%; H = 12.45%; N = 4.68%; O = 10.69% |
| solubility in organic solvents | hot methanol, $CHCl_3$, DMSO |
| water solubility | insoluble |
| melting point | 94–95° C. |
| TLC | chloroform/methanol 9:1 $R_f = 0.75$ |

EXAMPLE 2-PREPARATION OF N,N-BIS(2-HYDROXYETHYL)-PALMITAMIDE

A solution of 2.75 g palmitoyl chloride (10 mmol) in 20 ml anhydrous ethylether is added drop by drop in 30 minutes to a solution of 2.2 g diethanolamine (21 mmol) in 50 ml methanol and 100 ml anhydrous ethyl ether under continuous stirring at 0° C.

The resulting mixture is maintained under stirring for 1 hour at 0° C., and successively for 5 hours at room temperature. The suspension thus obtained is evaporated to dryness, the raw residue is crystallized from 25 ml 80% ethanol, the product is separated by filtration, washed three times with 5 ml 80% ethanol, and finally dried under high vacuum.

The reaction yield is about 78%. The physical-chemical properties of N,N-bis(2-hydroxyethyl)-palmitoylamide product are the following:

| | |
|---|---|
| physical state | white crystalline powder |
| raw formula | $C_{20}H_{41}NO_3$ |
| molecular weight | 343.56 |
| elemental analysis | C = 69.92%; H = 12.039; N = 4.47%; O = 13.97% |
| organic solvent solubility | >10 mg/ml in DMSO |
| water solubility | poorly soluble |
| melting point | 66.5–67.5° C. |
| TLC | eluent chloroform/methanol 95:5 $R_f = 0.21$ |

EXAMPLE 3-PREPARATION OF N-(2-HYDROXYPROPYL)-PALMITAMIDE

A mixture of 2.57 g palmitic acid (10 mmol) and 1.13 g 2-hydroxypropylamine (15 mmol) is charged into a flask fitted with a reflux condenser, and heated by means of an oil bath to 160° C. for 6 hours. The reaction mixture is then directly crystallized from 50 ml ethanol at 95°, the crystallized product is then separated by filtration, washed three times with 10 ml ethanol at 95°, and finally dried under high vacuum. The reaction yield is about 80%.

The physical-chemical properties of N-(2- hydroxypropyl)-palmitamide product are the following:

| | |
|---|---|
| physical state | white crystalline powder |
| raw formula | $C_{19}H_{39}NO_2$ |
| molecular weight | 313.53 |
| elemental analysis | C = 72.79%; H = 12.54%; N = 4.47%; O = 10.21% |
| organic solvent solubility | >3 mg/ml in DMSO; >10 mg/ml in n-octanol |
| water solubility | poorly soluble |
| melting point | 91–93° C. |
| TLC | eluent chloroform/methanol 95:5 $R_f = 0.40$ |

EXAMPLE 4-PREPARATION OF N-(2-HYDROXYETHYL)-STEAROYLAMIDE

A mixture of 2.85 g stearic acid (10 mmol) and 0.916 g ethanolamine (15 mmol) is charged into a flask fitted with a reflux condenser, and heated by means of an oil bath to 160° C. for 6 hours.

The reaction mixture is then directly crystallized from 50 ml ethanol at 95°, the crystallized product is then separated by filtration, washed three times with 10 ml ethanol at 95°, and finally dried under high vacuum. The reaction yield is about 90%.

The physical-chemical properties of N-(2- hydroxyethyl)-stearoylamide product are the following:

| | |
|---|---|
| physical state | white crystalline powder |
| raw formula | $C_{20}H_{41}NO_2$ |
| molecular weight | 327.55 |
| elemental analysis | C = 73.34%; H = 12.62%; N = 4.28%; O = 9.77% |
| organic solvent solubility | >5 mg/ml in chloroform |
| water solubility | poorly soluble |
| melting point | 98–100° C. |
| TLC | eluent chloroform/methanol/water 28% $NH_3$ 80:25:2:1 $R_f = 0.87$ |

EXAMPLE 5-PREPARATION OF N-(2-HYDROXYETHYL)-LAUROYLAMIDE

A mixture of 2.00 g lauric acid (10 mmol) and 0.916 g ethanolamine (15 mmol) is charged into a flask fitted with a reflux condenser, and heated by means of an oil bath to 160° C. for 6 hours . The reaction mixture is then directly crystallized from 50 ml 80% ethanol, the crystallized portion is then separated by filtration, washed three times with 10 ml cool 80% ethanol, and finally dried under high vacuum.

The reaction yield is about 90%.

The physical-chemical properties of N-(2- hydroxyethyl)-lauroylamide product are the following:

| | |
|---|---|
| physical state | white crystalline powder |
| raw formula | $C_{14}H_{29}NO_2$ |
| molecular weight | 243.39 |
| elemental analysis | C = 69.09%; H = 12.01%; N = 5.76%; O = 13.15% |
| water solubility | poorly soluble |
| organic solvent solubility | >10 mg/ml in DMSO; >10 mg/ml in chloroform |
| melting point | 85–87° C. |
| TLC | eluent chloroform/methanol/water/ 28% $NH_3$ 80:25:2:1 $R_f = 0.83$ |

EXAMPLE 6-PREPARATION OF N,N-BIS(2-HYDROXYETHYL)-LAUROYLAMIDE

A solution of 2.19 g lauroyl chloride (10 mmol) in 20 ml anhydrous ethylether is added drop by drop in 30 minutes to a solution of 2.2 g diethanolamine (21 mmol) in 50 ml methanol and 100 ml anhydrous ethyl ether under continous stirring at 0° C.

The resulting mixture is maintained under stirring for 1 hour at 0° C., and successively for 5 hours at room temperature. The suspension thus obtained is evaporated to dryness, the raw residue is crystallized from 25 ml 80% ethanol, the product is separated by filtration, washed three times with 5 ml 80% ethanol, and finally dried under high vaccum.

The reaction yield is about 88%. The physical-chemical properties of N,N -bis(2-hydroxyethyl)-lauroylamide product are the following:

| | |
|---|---|
| physical state | white crystalline powder |
| raw formula | $C_{16}H_{33}NO_3$ |
| molecular weight | 287.44 |
| elemental analysis | C = 66.86%; H = 11.57%; N = 4.87%; O = 16.70% |
| organic solvent solubility | >10 mg/ml in DMSO; >10 mg/ml in chloroform |
| water solubility | poorly soluble |
| melting point | 47–49° C. |
| TLC | eluent chloroform/methanol/water/ 28% $NH_3$ 80:25:2:1 $R_f = 0.80$ |

EXAMPLE 7-PREPARATION OF N-(2-HYDROXYETHYL)-4-HYDROXYBUTIRRAMIDE

A mixture of 0.861 g gammabutirrolactone (10 mmol) and 1.22 g ethanolamine (20 mmol) is charged into a flask fitted with a reflux condenser, and heated by means of an oil bath to 60° C. for 6 hours. 50 ml ethanol are added and the resulting solution is eluted through a column containing 20 ml of [H⁺] sulfonic resin Dowex 50×8, the eluate is evaporated to dryness and the oil thus obtained is dried under high vacuum.

The reaction yield is about 78%.

The physical-chemical properties of N-(2-hydroxyethyl)-4-hydroxybutirramide product are the following:

| | |
|---|---|
| physical state | deliquescent solid at room temperature |
| raw formula | $C_6H_{13}NO_3$ |
| molecular weight | 147.7 |
| elemental analysis | C = 48.97%; H = 8.90%; N = 9.52%; O = 32.61% |
| organic solvent solubility: | >10 mg/ml in DMSO; >10 mg/ml in ethanol |
| water solubility | >10 mg/ml |
| melting point | / |
| TLC | eluent chloroform/methanol/water/28% $NH_3$ 80:25:2:1 $R_f = 0.73$ |

EXAMPLE 8-PREPARATION OF N-(2-HYDROXYETHYL)-BENZOYLAMIDE

A solution of 1.41 g benzoyl chloride (10 mmol) in 20 ml anhydrous ethylether is added drop by drop in 30 minutes to a solution of 1.24 g ethanolamine (21 mmol) in 50 ml methanol and 100 ml anhydrous ethyl ether under continous stirring at 0° C.

The resulting mixture is maintained under stirring for 1 hour at 0° C., and successively for 5 hours at room temperature. The suspension thus obtained is evaporated to dryness, the raw residue is suspended in 50 ml water and extracted exhaustively with ethylacetate in a liquid-liquid continuous extractor. The ethylacetate solution is dried on sodium sulfate and concentrated to about 20 ml. The product is then crystallized by adding 30 ml ethylether, and it is separated by filtration and dried under high vacuum.

The reaction yield is about 90%.

The physical-chemical properties of N,N-bis(2-hydroxyethyl)-benzoylamide product are the following:

| | |
|---|---|
| physical state | white crystalline powder |
| raw formula | $C_9H_{11}NO_2$ |
| molecular weight | 165.19 |
| elemental analysis | C = 65.44%; H = 6.71%; N = 8.48%; O = 19.37% |
| organic solvent solubility | >10 mg/ml in ethanol; >10 mg/ml in DMSO |
| water solubility | >10 mg/ml |
| melting point | 63–65° C. |
| TLC | eluent chloroform/methanol/water/28% $NH_3$ 80:25:2:1 $R_f = 0.67$ |

EXAMPLE 9-PREPARATION OF N,N-BIS-(2-HYDROXYETHYL)-BENZOYLAMIDE

A solution of 1.41 g benzoyl chloride (10 mmol) in 20 ml anhydrous ethyl ether is added drop by drop in 30 minutes to a solution of 2.21 g diethanolamine (21 mmol) in 50 ml methanol and 100 ml anhydrous ethyl ether under continous stirring at 0° C.

The resulting mixture is maintained under stirring for 1 hour at 0° C., and successively for 5 hours at room temperature. The suspension thus obtained is evaporated to dryness, the raw residue is suspended in 50 ml water and extracted exhaustively with ethylacetate in a liquid-liquid continuous extractor. The ethylacetate solution is dried on sodium sulfate and concentrated to about 20 ml. The product is then crystallized by adding 30 ml ethylether, and it is separated by filtration and dried under high vacuum.

The reaction yield is about 90%.

The physical-chemical properties of N,N-bis(2-hydroxyethyl)-lauroylamide product are the following:

| | |
|---|---|
| physical state | white crystalline powder |
| raw formula | $C_{11}H_{15}NO_3$ |
| molecular weight | 209.25 |
| elemental analysis | C = 63.14%; H = 7.22%; N = 6.69%; O = 22.94% |
| organic solvent solubility | >10 mg/ml in ethanol; >10 mg/ml in DMSO |
| water solubility | >10 mg/ml |
| melting point | 62–64° C. |
| TLC | eluent chloroform/methanol/water/28% $NH_3$ 80:25:2:1 $R_f = 0.65$ |

EXAMPLE 10-PREPARATION OF N,N-BIS(2-HYDROXYETHYL)-OLEOYLAMIDE

A solution of 3.00 g oleoyl chloride (10 mmol) in 20 ml anhydrous ethylether is added drop by drop in 30 minutes to a solution of 2.2 g diethanolamine (21 mmol) in 50 ml methanol and 100 ml anhydrous ethyl ether under continuous stirring at 0° C.

The resulting mixture is maintained under stirring for 1 hour at 0° C., and successively for 5 hours at room temperature. The suspension thus obtained is evaporated to dryness, the raw residue is suspended in 25 ml water and extracted with 50 ml chloroform. The organic phase is washed twice with 50 ml $Na_2CO_3$ 0.1M, twice with 50 ml HCl 0.1M, twice with water, dried on sodium sulfate and finally evaporated. The oily product thus obtained is dried under high vacuum.

The reaction yield is about 75%.

The physical-chemical properties of N,N-bis(2-hydroxyethyl)-oleoylamide product are the following:

| | |
|---|---|
| physical state | oily liquid |
| raw formula | $C_{22}H_{43}NO_3$ |
| molecular weight | 369.61 |
| elemental analysis | C = 71.45%; H = 11.75; N = 3.80%; O = 13.0% |
| organic solvent solubility | >10 mg/ml in DMSO; >10 mg/ml in chloroform |
| water solubility | poorly soluble |
| melting point | / |
| TLC | eluent chloroform/methanol/water/28% $NH_3$ 80:25:2:1 $R_f = 0.95$ |

EXAMPLE 11-PREPARATION OF N,N-BIS-(2-HYDROXYETHYL)-LINOLEOYLAMIDE

A solution of 2.87 g isobutylchloroformiate (21 mmol) in 50 ml THF is slowly added drop by drop in 30 minutes to a mixture of 5.61 g linoleic acid (20 mmol) and 2.13 g triethylamine (21 mmol) in 150 ml anhydrous THF under stirring at −10° C.

The obtained mixture is maintained under stirring for 2 hours at −10° C., and successively for 15 hours at 0° C.

3.5 g diethanolamine are then slowly added drop by drop in 30 minutes.

After the reaction is left under stirring at 0°C. for further 6 hours it is evaporated to dryness. The raw residue is suspended in 25 ml water and extracted with 50 ml chloroform; the organic phase is washed twice with 50 ml Na$_2$CO$_3$ 0.1M, twice with 50 ml HCl 0.1 M, twice with 50 ml water, dried on sodium sulfate and finally evaporated to dryness. The oily product thus obtained is dried under high vacuum.

The reaction yield is about 70%.

The physical-chemical properties of N,N-bis(2-hydroxyethyl)-linoleoylamide product are the following:

| | |
|---|---|
| physical state | oily liquid |
| raw formula | C$_{22}$H$_{41}$NO$_3$ |
| molecular weight | 367.61 |
| elemental analysis | C = 71.80%; H = 11.30; N = 3.80%; O = 13.1% |
| organic solvent solubility | >10 mg/ml in ethanol; >10 mg/ml in chloroform |
| water solubility | poorly soluble |
| melting point | / |
| TLC | eluent chloroform/methanol/water/ 28% NH$_3$ 80:25:2:1 R$_f$ = 0.95 |

EXAMPLE 12-PREPARATION OF N-(2-HYDROXYETHYL)-DESOXYCHOLAMIDE

A solution of 1.5 g isobutylchloroformiate (11 mmol) in 40 ml DMF are slowly added drop by drop in 30 minutes to 4.15 g sodium desoxycholate (10 mmol) in 40 ml DMF under stirring at −10° C. The mixture is left under stirring at −10° C. for 2 hours and successively for 15 hours at 0° C. 1.22 g ethanolamine are then slowly added drop by drop in 30 minutes.

After the reaction is maintained under stirring for further 6 hours at 0° C., 100 ml water are added to it, a precipitate forms which is separated by filtration, washed with water and dried under vacuum.

The raw product thereby obtained is solubilized in ethanol, precipitated by adding cool water and finally dried under high vacuum.

The physical-chemical properties of N-(2-hydroxyethyl)-desoxycholamide product are the following:

The reaction yield is about 90%.

| | |
|---|---|
| physical state | white amorphous powder |
| raw formula | C$_{26}$H$_{45}$NO$_4$ |
| molecular weight | 435.65 |
| elemental analysis | C = 71.68%; H = 10.41%; N = 3.22%; O = 14.69% |
| organic solvent solubility | >10 mg/ml in DMSO |
| water solubility | poorly soluble |
| melting point | / |
| TLC | eluent chloroform/methanol/water/ 28% NH$_3$ 80:25:2:1 R$_f$ = 0.61 |

EXAMPLE 13-PREPARATION OF N-(2-HYDROXYETHYL)-SALICYLAMIDE

A mixture of 1.52 g methylsalicylate (10 mmol) and 1.22 g ethanolamine (20 mmol) is charged into a flask fitted with a reflux condenser, and heated by means of an oil bath to 60° C. for 60 hours. 50 ml ethanol are added and the resulting solution is eluted through a column containing 20 ml of [H$^+$] sulfonic resin Dowex 50×8, the eluate is evaporated to dryness. The residue is crystallized from 30 ml cool water, and the solid product obtained is separated by filtration, washed three times with 10 ml cool water and finally dried under high vacuum.

The reaction yield is about 70 %.

The physical-chemical properties of N-(2-hydroxyethyl)-salicylamide product are the following:

| | |
|---|---|
| physical state | white crystalline powder |
| raw formula | C$_9$H$_{11}$NO$_3$ |
| molecular weight | 181.19 |
| elemental analysis | C = 59.66%; H = 6.12%; N = 7.73%; O = 26.49% |
| organic solvent solubility | >10 mg/ml in ethanol |
| water solubility | >poorly soluble |
| melting point | 113–115° C. |
| TLC | eluent chloroform/methanol/water/ 28% NH$_3$ 80:25:2:1 R$_f$ = 0.66 |

EXAMPLE 14-PREPARATION OF N-(2-HYDROXYETHYL)-ISONICOTINAMIDE

A mixture of 1.37 g methylisonicotinate (10 mmol) and 1.22 g ethanolamine (20 mmol) is charged into a flask fitted with a reflux condenser, and heated by means of an oil bath to 60° C. for 60 hours. 50 ml 80% ethanol are added and the resulting solution is eluted through a column containing 20 ml of [H$^+$] sulfonic resin Dowex 50×8, the eluate is evaporated to dryness. The residue is crystallized from 30 ml isopropanol, and the product obtained is separated by filtration, washed three times with 10 ml cool isopropanol and finally dried under high vacuum.

The reaction yield is about 85%.

The physical-chemical properties of N-(2-hydroxyethyl)-isonicotinamide product are the following:

| | |
|---|---|
| physical state | white crystalline powder |
| raw formula | C$_8$H$_{10}$N$_2$O$_2$ |
| molecular weight | 166.18 |
| elemental analysis | C = 57.82%; H = 6.07%; N = 16.86%; O = 19.26% |
| organic solvent solubility | >10 mg/ml in methanol |
| water solubility | >10 mg/ml |
| melting point | 136–138° C. |
| TLC | eluent chloroform/methanol/water/ 28% NH$_3$ 80:25:2:1 R$_f$ = 0.59 |

EXAMPLE 15-PREPARATION OF N-(2-HYDROXYETHYL)-DL-α-LIPOAMIDE

A solution of 2.87 g isobutylchloroformiate (21 mmol) in 50 ml THF is slowly added drop by drop in 30 minutes to a mixture of 4.13 g DL-α-lipoic acid (20 mmol) and 2.13 g of triethylamine (21 mmol) in 100 ml anhydrous THF under stirring at −10° C.

The obtained mixture in maintained under stirring for 2 hours at −10° C., and successively for 15 hours at 0° C.

1.8 g ethanolamine are then slowly added drop by drop in 30 minutes.

After the reaction is left under stirring at 0° C. for further 6 hours it is evaporated to dryness. The raw residue is purified by chromatography on a silica gel column, using as the eluent a mixture of chloroform and methanol respectively in volumetric ratio 90:10. The eluate fractions containing the desired product are collected, evaporated to dryness and the residue obtained is evaporated under high vacuum. The reaction yield is about 70%.

The physical-chemical properties of N-(2-hydroxyethyl)-DL-α α-lipoamide product are the following:

| | |
|---|---|
| physical state | yellow thick oil |
| raw formula | $C_{10}H_{19}NO_2S_2$ |
| molecular weight | 249.39 |
| elemental analysis | C = 48.16%; H = 7.68%; N = 5.62%; O = 12.83%; S = 25.71% |
| organic solvent solubility | >10 mg/ml in ethanol |
| water solubility | >10 mg/ml |
| melting point | / |
| TLC | eluent chloroform/ methanol/water/ 28% $NH_3$ 80:25:2:1 $R_f = 0.80$ |

EXAMPLE 16-PREPARATION OF N-(2 HYDROXYETHYL)-PENTADECANAMIDE

A mixture of 2.43 g of pentadecanoic acid (10 mmol) and 0.916 g of ethanolamine (15 mmol) is charged into a flask fitted with a reflux condenser and heated by means of an oil bath to 160° C. for 6 hours. The reaction mixture is then directly crystallized from 50 ml of acetone. The crystallized portion is then separated by filtration, washed three times with 10 ml cool acetone and finally dried under high vacuum.

The reaction yield is about 92%.

The physical chemical properties of N-(2-hydroxyethyl)-pentadecanamide are the following:

| | |
|---|---|
| physical state | white crystalline powder |
| raw formula | $C_{17}H_{35}NO_2$ |
| molecular weight | 285.47 |
| elemental analysis | C = 71.53%; H = 12.36%; N = 4.91% O = 10.21% |
| water solubility | poorly soluble |
| organic solvent solubility | >5 mg/ml in DMSO; >10 mg/ml in N-octanol |
| melting point | 95.8–96.7° C. |
| TLC | eluent chloroform/metanolo, 95:5, Rf = 0.35 |

EXAMPLE 17-PREPARATION OF N-(2 HYDROXYETHYL)-EPTADECANAMIDE

A mixture of 2.71 g of eptadecanoic acid (10 mmol) and 0.916 g of ethanolamine (15 mmol) is charged into a flask fitted with a reflux condenser and heated by means of an oil bath to 160° C. for 6 hours. The reaction mixture is then directly crystallized from 50 ml 95° ethanol. The crystallized portion is then separated by filtration, washed three times with 10 ml cool 95° ethanol and finally dried under high vacuum.

The reaction yield is about 92%.

The physical chemical properties of N-(2 hydroxyethyl) - eptadecanamide are the following:

| | |
|---|---|
| physical state | white crystalline powder |
| raw formula | $C_{10}H_{39}NO_2$ |
| molecular weight | 313.53 |
| elemental analysis | C = 72.79%; H = 12.54%; N = 4.74%; O = 10.21%. |
| water solubility | poorly soluble |
| organic solvent solubility | >5 mg/ml in DMSO; >10 mg/ml in N-octanol |
| melting point | 100–102° C. |
| TLC | eluent chloroform/methanol, 95:5 $R_f = 0.35$ |

EXAMPLE 18-PREPARATION OF N-(2 HYDROXYETHYL)-ACETAMIDE

A mixture of 0.60 g of acetic acid (10 mmol) and 0.916 g of ethanolamine (15 mmol) is charged into a flask fitted with a reflux condenser and heated by means of an oil bath to 160° C. for 6 hours. The reaction mixture is then subjected to a fractional distillation under perfect vacuum through Vigreux column. The distillate fraction must be collected at 145°–147° C. (2.5 mm Hg).

The reaction yield is about 85%.

The physical chemical properties of N-(2 hydroxyethyl)acetamide are the following:

| | |
|---|---|
| physical state | clear uncoloured liquid |
| raw formula | $C_4H_9NO_2$ |
| molecular weight | 103.12 |
| elemental analysis | C = 46.59%; H = 8.80%; N = 13.58%; O = 31.03%. |
| water solubility | >10 mg/ml |
| organic solvent solubility | >10 mg/ml in DMSO; >10 mg/ml in ethanol |
| melting point | / |
| TLC | eluent chloroform/methanol/water/ 28% $NH_3$, 80:25:2:1 Rf = 0.51 |

EXAMPLE 19-PREPARATION OF N-(2 HYDROXYETHYL)-MYRISTOYLAMIDE

A mixture of 2.43 g of methylmyristate (10 mmol) and 0.916 g of ethanolamine (15 mmol) is charged into a flask fitted with a reflux condenser and heated by means of an oil bath to 160° C. for 6 hours. The reaction mixture is then directly crystallized from 50 ml cool methanol. The crystallized portion is then separated by filtration, washed three times with 10 ml cool methanol and finally dried under high vacuum.

The reaction yield is about 85%.

The physical chemical properties of N-(2 hydroxyethyl)myristoylamide are the following:

| | |
|---|---|
| physical state | white crystalline powder |
| raw formula | $C_{16}H_{33}NO_2$ |
| molecular weight | 271.45 |
| elemental analysis | C = 70.80%; H = 12.25%; N = 5.16%; O = 11.79%. |
| water solubility | poorly soluble |
| organic solvent solubility | >5 mg/ml in DMSO; >10 mg/ml in n-octanol |
| melting point | 92–94° C. |
| TLC | eluent chloroform/methanol/water/ |

EXAMPLE 20-PREPARATION OF N-(2 HYDROXYETHYL)-NICOTINAMIDE

A mixture of 1.34 g of methylnicotinate (10 mmol) and 0.916 g of ethanolamine (15 mmol) is charged into a flask fitted with a reflux condenser and heated by means of an oil bath to 60° C. for 1 hour. The reaction mixture is then directly crystallized from 15 ml cool isopropanol. The crystallized portion is then separated by filtration, washed three times with 5 ml cool isopropanol and finally dried under high vacuum.

The reaction yield is about 88%.

The physical chemical properties of N-(2 hydroxyethyl)-nicotinamide are the following:

| | |
|---|---|
| physical state | deliquescent solid at room temperature |
| raw formula | $C_8H_{10}N_2O_2$ |
| molecular weight | 166.18 |
| elemental analysis | C = 57.82%; H = 6.07%; N = 16.86%; O = 19.26%. |
| water solubility | >10 mg/ml |
| organic solvent solubility | >10 mg/ml in DMSO; >10 mg/ml in methanol |
| melting point | 80° C.–90° C. |
| TLC | eluent chloroform/methanol/water 28% $NH_3$ 80:25:2:1 Rf = 0.60 |

EXAMPLE 21-PREPARATION OF N-(2-HYDROXYETHYL-10-UNDECENOYLAMIDE

A mixture of 1.84 g of 10-undecenoic acid (10 mmol) are solubilized in 30 ml of anhydrous methanol. Then 2 g of anhydrous solfonic resin Dowex 50×80 H+ are added; the mixture is left under stirring at 30° C. for 72 hours. After separation from the resin, the solution is dried by evaporation and the dry residue is added with 0.916 g of ethanolamine (15 mmol) for 20 hours at 60° C. The reaction mixture is then directly crystallized from 50 ml of methanol/water 2:1; the crystallized portion is then separated by filtration, washed three times with 10 ml cool water and finally dried under high vacuum.

The reaction yield is about 70%.

The physical chemical properties of N-(2 hydroxyethyl)-10-undecenoylamide are the following:

| | |
|---|---|
| physical state | white crystalline powder |
| raw formula | $C_{13}H_{25}NO_2$ |
| molecular weight | 227.35 |
| elemental analysis | C = 68.68%; H = 11.08%; N = 6.16%; O = 14.07%. |
| water solubility | poorly soluble |
| organic solvent solubility | >10 mg/ml in DMSO; >10 mg/ml in ethanol |
| melting point | 68.5° C.–70.5° C. |
| TLC | eluent chloroform/methanol/water 28% $NH_3$ 88:25:2:1 Rf = 0.79 |

EXAMPLE 22-PREPARATION OF N-(2 HYDROXYETHYL)-ACETYL SALICYLAMIDE

A solution of 1.99 g acetylsalicyl chloride (10 mmol) in 20 ml anhydrous acetonitrile was slowly poured drop by drop for 30 min. into a solution of 1.28 g of ethanolamine (21 mmol) in 50 ml anhydrous acetonitrile under stirring at 0° C.

The mixture obtained was kept under stirring for 1 hour at 0° C. and then for 5 hours at room temperature and finally dried by evaporation. The residue is cristallyzed from 20 ml of water.

The crystallized portion is then separated by filtration, washed three times with 10 ml cool water and finally dried under high vacuum.

The reaction yield is about 70%.

The physical chemical properties of N-(2 hydroxyethyl)-acetyl salicylamide are the following:

| | |
|---|---|
| physical state | white crystalline powder |
| raw formula | $C_{11}H_{13}NO_4$ |
| molecular weight | 223.23 |
| elemental analysis | C = 59.19%; H = 5.87%; N = 6.27%; O = 28.67% |
| water solubility | poorly soluble |
| organic solvent solubility | >10 mg/ml in DMSO; >10 mg/ml in ethanol |
| melting point | 96–99° C. |
| TLC | eluent chloroform/methanol/water acetic acid 80:25:2:1 Rf = 0.93 |

EXAMPLE 23-PREPARATION OF N,N-BIS-(2 HYDROXYETHYL)-DESOXYCHOLAMIDE

A solution of 4.15 g sodium desoxycholate (10 mmol) in 40 ml anhydrous DMF is prepared and set under agitation at −10° C., then a solution of 1.5 g isobutylchloroformiate (11 mmol) in 10 ml DMF was slowly poured drop by drop during 30 minutes. The reaction is left under stirring for 2 hours at −10° C. and successively for 15 hours at 0° C.

2.0 g of diethanolamine are then slowly added drop by drop over 30 minutes. The reaction is left under stirring at 0° C. for further 6 hours and 100 ml of water are added: the obtained precipitate is separated by filtration, washed with water and vacuum dried. The raw product is solubilized in ethanol, precipitated by cool water and finally dried under high vacuum.

The reaction yield is about 88%.

The physical chemical properties of N,N-bis-(2-hydroxyethyl)-desoxycholamide are the following:

| | |
|---|---|
| physical state | white amorphous powder |
| raw formula | $C_{28}H_{49}NO$ |
| molecular weight | 479.71 |
| elemental analysis | C = 70.11%; H = 10.30%; N = 2.92%; O = 16.68% |
| water solubility | poorly soluble |
| organic solvent solubility | >10 mg/ml in DMSO; |
| melting point | / |
| TLC | eluent chloroform/methanol/water 28% $NH_3$, 80:25:2:1, Rf = 0.59 |

EXAMPLE 24-PREPARATION OF N-(2 HYDROXYETHYL)-BUTIRAMIDE

A mixture of 0.88 g of butiric acid (10 mmol) and 0.916 g of ethanolamine (15 mmol) is charged into a flask fitted with a reflux condenser and heated by means of an oil bath to 160° C. for 6 hours. The reaction mixture is then subjected to fractional distillation under vacuum in Vigreux Column. The portion which distilled at 154°–156° C. (30 mm/Hg) is finally collected.

The reaction yield is about 85%.

The physical chemical properties of N-(2-hydroxyethyl)-butiramide are the following:

| | |
|---|---|
| physical state | deliquescent solid |
| raw formula | $C_6H_{13}NO_2$ |
| molecular weight | 131.18 |
| elemental analysis | C = 54.94%; H = 9.99%; N = 10.68%; O = 24.39%. |
| water solubility | >10 mg/ml |
| organic solvent solubility | >10 mg/ml in DMSO; >10 mg/ml in ethanol |
| melting point | / |
| TLC | eluent chloroform/methanol/water 28% $NH_3$, 80:25:2:1, Rf = 0.69 |

EXAMPLE 25-PREPARATION OF N-(2-HYDROXYETHYL) ARACHIDONYLAMIDE

A mixture of 3.04 g arachidonic acid (10 mmol) and 10.6 g triethylamine (10.5 mmol) in 100 ml anhydrous THF placed under stirring under nitrogen atmosphere, is slowly added drop by drop in 30 minutes to a solution 1.44 g isobutylchloroformiate (10.5 mmol) in 50 ml THF. The resulting mixture is kept under stirring for 2 hours at −10° C. and then for 5 hours at 0° C. Then 0.9 g ethanolamine are slowly added drop by drop and the obtained mixture is kept under stirring for further 2 hours at 0° C. and then evaporated to dryness. The raw residue is purified by gel chromatography using as the eluent a mixture of chloroform and methanol 98:2 v/v. The different fractions of eluate are then collected and evaporated to dryness and the residue is dried under vacuum.

The physical chemical properties of N-(2-hydroxyethyl)-arachidonylamide are the following:

| | |
|---|---|
| physical state | uncoloured oil |
| raw formula | $C_{22}H_{37}NO_2$ |
| molecular weight | 347.54 |
| elemental analysis | C = 76.03%; H = 10.73%; N = 4.03%; O = 9.21%. |
| water solubility | poorly soluble |
| organic solvent solubility | >10 mg/ml in DMSO; >10 mg/ml in ethanol |
| melting point | / |
| TLC | eluent chloroform/methanol/water 28% $NH_3$, 80:25:2:1, Rf = 0.66 |

EXAMPLE 26-PREPARATION OF N'-(2-HYDROXYETHYL)-4-AMINOBENZAMIDE

A solution of 1.44 g isobutylchloroformiate (10.5 mmol) in 10 ml DMF is slowly added drop by drop in 30 minutes to a mixture 1.37 g triethylamine (10 mmol) in 50 ml anhydrous DMF under stirring at −10° C., and successively for 5 hours at 0° C.

0.9 g ethanolamine are then slowly added drop by drop in 10 minutes. After further 2 hours at 0° C. under stirring, the mixture is evaporated to dryness. The raw residue is purified by chromatography through silica gel column using as eluent a mixture of chloroform/methanol 30% $NH_3$ respectively in volumetric ratio 90:9:1. The eluate fraction containing the desired pure product are collected and concentrated under vacuum; the residue is solubilized in 5 ml water and lyophilized.

The reaction yield is about 80%.

The physical-chemical properties of N'-(2-hydroxyethyl)-4-aminobenzamide are the following:

| | |
|---|---|
| physical state | white amorphous powder |
| raw formula | $C_9H_{12}N_2O_2$ |
| molecular weight | 181.21 |
| elemental analysis | C = 59.98%; H = 7.71%; N = 15.55%; O = 17.76% |
| water solubility | >10 mg/ml |
| organic solvent solubility | >10 mg/ml in DMSO |
| melting point | / |
| TLC | eluent chloroform/methanol/water/ 28% $NH_3$ 80:25:2:1, Rf = 0.54 |

EXAMPLE 27-PREPARATION OF N'-(2-HYDROXYETHYL)-4-AMINOBUTIRAMIDE 2.37 g of benzyloxicarbonyl-4-aminobutanoic acid (10 mmol) are solubilized in 50 ml anhydroius DMF with 1.01 g triethylamine (10 mmol). The solution is submitted to stirring at −10° C. and 1.44 g of isobutylchloroformiate (10.5 mM) in 10 ml DMF are slowly added drop by drop in 30 minutes.

The mixture is kept under stirring for 2 hours at −10° C. and successively for 5 hours at 0° C. 0.9 g of ethanolamine are then slowly added drop by drop in 10 minutes. After further 2 hours under stirring at 0° C., the mixture is evaporated to dryness. The raw residue is risuspended using 50 ml glacial acetic acid and submitted to hydrogen stream for 20 hours in the presence of black palladium powder. The catalyst is then removed by filtration and the solution evaporated to dryness. The raw residue is resuspended in 100 ml ethanol/water 1:1 and eluted through a column containing 20 ml [OH⁻] resin Dowex 1×8 cooled to 0° C. The eluate is concentrated to about 3 ml and purified by chromatography through a column containing Lichrosorb RP-18 resin (Merck) using as the eluent a water/ethanol mixture; the fractions containing the desired product are collected and concentrated under vacuum; the residue is then lyophilized.

The reaction yield is about 80%.

The chemical-physical characteristics of N'-(2-hydroxyethyl)-4-aminobutiramide are the following:

| | |
|---|---|
| physical state | white amorphous powder |
| raw formula | $C_6H_{14}N_2O_2$ |
| molecular weight | 146.19 |
| elemental analysis | C = 49.30%; H = 6.65%; N = 19.16%; O = 21.89%. |
| water solubility | >10 mg/ml |
| organic solvent solubility | >10 mg/ml in DMSO |
| melting point | / |
| TLC | eluent chloroform/methanol/water 28% $NH_3$ 80:25:2:1, Rf = 0.10 eluent ethanol/water/acetic acid 70:20:10, |

BIOLOGICAL ACTIVITY

Part A - Assumption

As previously pointed out mast cell is a widespread cell in tissues where it is in anatomical and functional contiguity with nerve endings, particularly with those of peptidergic type.

Under physiological conditions mast cell is quiescent, but when activated by neurogenic or immunogenic stimuli, degranulates, releasing substances contained in its granules, some of these substances producing cytotoxic effects. Mast cell and some substances released from same are strictly correlated to autoimmune pathologies.

This type of pathologies are characterized by autoaggressive processes mediated by immunocompetent cells and among them mast cell. Due to its anatomo-functional configuration, mast cell acts as the final mediator of lesive processes at the expense of specific tissues, being characteristic of autoimmune pathologies.

This role, which may be elicited by residing mast cells, by hyperplasia or by an overstimulation on the modulation of the morphofunctional unit nerve-mast cell, is in any case mediated by the mutual interaction between mast cell and nervous system, in particular having peptidergic transmission (D. Johnson and W. Krenger, Neuroch. Res. 17 (9), 1992: 939–951).

In particular considering each specific autoimmune pathology it resulted from experimental evidence that the following mechanisms are involved.

1. Inflammatory Demyelinating Pathologies of the Central Nervous System

In patients affected by Multiple Sclerosis (MS) the presence of mast cells was demonstrated, which a key role was attributed to in the evolution of clinical symptomatology and in the same pathogenesis of this disease, since these cells are not present in not -demyelinated areas or in the corresponding cerebral regions of patients not affected by MS (J. Olsson,1974, Acta Neurol. Scandinav. 50, 611–618). MS etiology has not yet been completely explained, but this disease appears in genetically predisposed individuals as a reaction to "environmental" causes. This reaction may occur through different routes, being in any case ascribable to the release of substance P and to the expression of its receptor. Substance P contribute to increase the permeability to hematoencephalic barrier, facilitating the inlet of immunocompetent substances and the inflammation demyelination and gliosis processes: the presence of positive astrocytes due to the presence of the substance P in the plaques, implies a decisive role for the neurotransmitter not only at the onset of the plaques, but also during the whole disease course (R. Barker and A. Larner, 1992, Medical Hypothesis,37:40–43).

Evidences were also obtained on an experimental model of MS (Experimental Allergic Encephalomyelitis EAE), which confirmed that when this pathology is overt, an increase of degranulated mast cells is observed in the regions reached by the inflammatory process (Bo et al., 1991, J. of Neurological Sciences,105: 135–142).

2. Articular Pathologies

Rheumatoid Arthritis (RA) is a multisystemic autoimmune pathology involving the destruction of articular cartilage, tissue erosion, and persistent inflammatory synovitis. Synovia is a connective tissue, being densely vascularized and innervated by nervous peptidergic fibers, mainly substance P and Calcitonin Gene Relative Peptide (CGRP), whose levels increase during the inflammatory phase. This means that there is a causal correlation between the release of substance P and the inflammation associated with arthritis, probably mediated by the increase in the release of permeabilizing substances. Furthermore, in patients affected by chronic arthritis, an increase in the substance P levels corresponds to an increase of degranulated mast cells percentage (Aloe et al., Arthritis and Rheumatism, 1992, 35,3: 351–355).

A specific pathogenetic role of the substance P in this disease was also confirmed by carrying out experiments on synoviocytes of patients affected by RA (M. Lotz et al,. Science, 235: 893–895, 1987). Moreover, experiments carried out in carrageenin-induced arthritis in rat had shown a correlation between the alteration occurring in the human pathology and in this experimental model (Aloe et al. Rheumatology 1992 vol.12 pp 213–216 ).

3. Dermal Autoimmune Pathologies

In these pathologies the neuropeptides contained at the level of the sensorial cutaneous (SP and VIP) and autonomic (VIP) endings can be locally released by means of antidromic mechanisms, inducing mast cell hyperactivation and mediators release (Matsuda H. et al., The J. of Immunology 1412: 927–931, 1989; Yano H. J. of Clinical Investigation, 84: 1276–1286, 1989). This activation system is involved in the atopical dermatitis (Giannetti and Girolimoni, 1989, British Journal of Dermatology, 121:681–688) and in psoriasis, where the substance P is able to induce mast cells degranulation, besides mediating stressogen phenomena (Farber E. W. et al.,1991, Int. J. of Dermatology, 30 (1): 8–12), correlated to the pathology exacerbation. In fact in psoriasis mast cells degranulation was correlated to "recurrence" phenomena (C. Schubert, E. Christophers, Arch. Derm. Res., 1985, 277:352–358). The same mechanisms are involved also in Behcet's disease (Gilhar A.,1989, J. of the American Academy of dermatology 21(3), 547–552) and in pigmented urticaria (Irani A. M. A. et al., Allergy, 11(9):31–34, 1989) or in pemphigus forms(Levi-Schaffer et al., 1991, Acta Derm.Venereol., 71, 3:269–271; Goldstein I. M. et al., Immunol. Ser. 46:527–545,1989; Anhalt G. J. and Morrison L. H., 1991, J. of Autoimmuniyu 4,17–35).

Connected to the above an experimental model was set up, in which acute inflammation involving mast cell degranulation was induced by administering phorbol ester to animals (B. K. Wershill et al., 1988, The J. of Immunology, 140 (7): 2356–2360). This experimental condition reproduces one of the main mechanisms of dermal autoimmune pathologies, such as psoriasis and atopical dermatitis.

The same mechanisms, ascribable to neurogenic stimuli induced by substance P, are also involved in ophtalmic autoimmune pathologies such as the uveitis (Mochizuki M., 1986, Eye Science,2,4:245–248) and inflammatory type gastrointestinal autoimmune pathologies (K. A. Sharkey, Annals of the New York Academy of Sciences, 1992, vol.664; 425–441; R. Stead, Annals New York Acad. of Sciences 1992 ad.664: 443–455), in which the neurogenic mechanism is directly or undirectly involved.

In view of the above evidences, we have verified if the specific N-acylderivatives according to the present invention are able to limit mast cells degranulation induced by neurogenic stimuli (substance P) in vitro and in vivo, and successively we have verified if the compounds according to the present invention result effective in the treatment of the specific pathologies, Multiple sclerosis, Rheumatoid arthritis, and dermal autoimmune pathologies.

B) Experimental Part i) Biologic Activity Against Mast Cells Degranulation Induced Neurogenic Stimuli (Substance P)

In order to verify the specificity of the N-acyl derivatives to act as local autacoids when administered by exogenous route under conditions of degranulation induced by mast cells physiological stimuli the following biological tests were carried out both in vivo and in vitro as described hereinbelow.

In Vivo Biologic Tests: Topical and General Application 2 weeks old Sprague Dawley rats, provided by Charles River from Calco, were locally treated by intradermal injection on the auricular pinna with the compounds in question at the dose of 0.5 mg/kg, in a buffered aqueous solution at physiological pH.

After 10 minutes a local administration of the substance P ($10^{-4}$M), able to induce a mast cells degranulation response, was carried out still by intradermal route.

After 30' from the substance P administration the animals were sacrificed and the relative tissue samples (pinna) were taken, for an analysis of the morphological aspect of the mast cells residing in the connectival tissue after fixation and coloration of toluidine blue. The inhibition degree in mast cells degranulation in the tissues of the animals treated with the compounds under question, in comparison with that of animals treated only with the physiological degranulation factor (substance P) was considered as a parameter for the biological activity.

From the morphological analysis it resulted that whereas substance P induced a degranulation in the majority of mast cells, under pretreatment conditions with the compounds of the present invention a marked inhibition of this phenomenon was observed.

In table 1 the obtained results are reported.

TABLE 1

Effects of ethanolamine and diethanolamine N-acyl derivatives against the mast cells degranulation after intradermal administration at the dose of 0.5 mg/kg.

| substance | % of degranulated mast cells |
| --- | --- |
| solvent | 8 |
| substance P | 94 |
| N-palmitoylethanolamide + subst. P | 50 |
| N-palmitoyldiethanolamide + subst. P | 35 |

N-acylderivatives compounds or a phisiological solution (DMSO for non water soluble compound) were administered subcutaneously at the dose of 20 mg/kg in the back of 2-weeks old rats (Sprague Dawley, Charles River) followed 20 minutes later by s.c. administration of substance P (1 μl of 10-6M solution or saline in the ear pinna). After 30 minutes, the rats were sacrificed and the ear pinna removed for histological assessment of mast cell degranulation by counting the number of degranulated mast cells.
Biological activity parameter: % of degranulated mast cells.

TABLE 2

Effects of aminoalcohols N-acyl derivatives after subcutaneous administration of 20 mg/kg.

| substance | | degranulated mast cells |
| --- | --- | --- |
| solvent | | 12 |
| substance P | | 92 |
| N-palmitoylethanolamide | + subst. P | 65 |
| N-palmitoyldiethanolamide | + subst. P | 48 |
| N-palmitoylpropanolamide | + subst. P | 49.5 |
| N-stearoylethanolamide | + subst. P | 60 |
| N-lauroylethanolamide | + subst. P | 54 |
| N-lauroyldiethanolamide | + subst. P | 28 |
| N-benzoylethanolamide | + subst. P | 48.8 |
| N-benzoyldiethanolamide | + subst. P | 36.8 |
| N-oleoyldiethanolamide | + subst. P | 44 |
| N-linoleoyldiethanolamide | + subst. P | 71 |
| N-salicyloylethanolamide | + subst. P | 38 |

TABLE 2-continued

Effects of aminoalcohols N-acyl derivatives after subcutaneous administration of 20 mg/kg.

| substance | | degranulated mast cells |
| --- | --- | --- |
| N-(DL-α-lipoyl)ethanolamide | + subst. P | 40 |
| N-pentadecanoylethanolamide | + subst. P | 51.1 |
| N-undecanoylethanolamide | + subst. P | 34.9 |
| N-acetylsalicyloylethanolamide | + subst. P | 54.3 |
| N-desoxycholylethanolamide | + subst. P | 58.6 |
| N-butiroylethanolamide | + subst. P | 55 |
| N-nicotinoylethanolamide | + subst. P | 65.3 |

In Vitro Biologic Test

Peritoneal mast cells of rat were taken according to the standard methodology described by Lagunoff (1975, Tech. Biochem. Biophys. Morphol., 2, pp. 289–305).

The cells were then cultured in MEM which 10% fetal calf serum was added to and then incubated in a Haereus® incubator for 30 minutes.

The derivatives under question at the concentration of $10^{-5}$M were added to the incubation medium.

At the end of the incubation the physiological degranulation stimulus represented also in the case by the substance P (10–4M) was added.

The cells were then centrifugated in order to remove the supernatant formed by the incubation medium and were placed onto a slide after coloration with toluidine blue, for the analysis of the morphological aspect at the optical microcope.

Also under these conditions the parameter to be considered was the percentage of degranulated cells after stimulation with the Substance P.

The obtained results are indicated in Tab. 3

TABLE 3

Effect of ethanolamine and diethanolamine N-acylderivatives against in vitro mast cells.

| substance | degranulated mast cell % |
| --- | --- |
| substance P | 96 |
| N-palmitoylethanolamide + subst. P | 52 |
| N-palmitoyldiethanolamide + subst. P | 30 |

These results demonstrate that the derivatives according to the present invention are able to modulate the degranulation processes induced by neuroimmunogenic stimuli, when they are administered by both local and general exogenous route, when the degranulation process induced by the Substance P is being carried out.

ii) Effects of the N-Acylderivatives on Experimental Allergic Encephalitis (EAE)(Experimental Model for Multiple Sclerosis), Materials and Methods Two groups of 6 weeks old mice of B10.PL strain (n=4) are immunized with 1–9NacMBP, following Jiang H. et al.'s method (Science 256:1213, 1992) modified by replacing Freund's adjuvant with Titer Max.

Palmitoylethanolamide, previously suspended in 1.5% carboxymethylcellulose, was daily administered at the dose of 10 mg/kg/die, starting from the day of immunization ($t_0$).

Parameters

The neurologic damage was evaluated according to the scale described by Zamil S. (J. Exp.med, 162: 2107,1985).

Results

The neurologic symptomatology appears 10 days after the immunization, the treatment with palmitoylethanolamide retards the appearance of the symptomatology as it clearly results from FIG. 1.

iii) Effects of the N-Acyl Derivatives on Synovia Inflammation (Experimental Model for Rheumatoid Arthritis)

Materials and Methods

The acute inflammation of synovia was induced by intraarticular administration of 50 μl of 1% carragenin/articulation in adult rats (n=5).

Carrageenin injection induces inflammation with a progressive proliferation of fibroblasts with lymphocytes infiltration and mast cell increase, producing an increase of synovia weight accompanied by an increase in nerve growth factor NGF levels.

N-hydroxyethylbenzoylamide was solubilized in a physiological solution and intraarticularly administered at the dose of 20 μg/articulation 20 minutes before the irritating agent (carragenin).

Parameters

The ability of this compound to reduce the inflammation (measured as the synovia weight) and the numbers of degranulated masts cells are evaluated.

Results

As it clearly appears from table 4 N-hydroxyethylbenzoylamide is able to reduce inflammation, limiting the increase in synovia weight and the numbers of degranulted mast cells.

Table 4- Protective effect of N-(2-hydroxyethyl)-benzoylamide on arthritis induced by carragenin in adult rats (n=5).

N-(2-hydroxyethyl)salicylamide is able to reduce the PMA acute inflammation, both at 1 and 5% concentrations exhibiting a dose-dependent effect.

The results are reported in Table 5.

TABLE 5

N-(2 hydroxyethyl)salicylamide effect on phorbol-12-myristate, 13-acetate (PMA) acute oedema.

| | Change in ear thickness at different times (hrs) (inches ± SEM) | | |
|---|---|---|---|
| | 12 | 24 | 48 |
| N-(2 hydroxyethyl) salicylamide | 1 ± 1 | 2 ± 1.5 | 2 ± 1 |
| PMA | 130 ± 1 | 130 ± 3 | 60 ± 3 |
| N-(2 hydroxyethyl) salicylamide 1% + PMA | 80 ± 5 | 70 ± 10 | 30 ± 4 |
| N (2 hydroxyethyl) salicylamide 5% + PMA | 80 ± 1 | 40 ± 2 | 25 ± 2 |

The administration routes encompassed in both human and animal pathologies which can be treated according to the present invention are the topical route, the intra- and trans-dermal route, the intraarticular route, the intracerebroventricular route, the corneal topical route, the intra- and retro-bulbar route, the vaginal route, as well as the topical route on the gastric mucous membrane, the intranasal and the inhaling route, and all the systemic administrations, and among them the oral route and the parenteral (intravenous, subcutaneous and intramuscular route).

Both for human and veterinary use the necessary doses to have therapeutic effectiveness depends on the administration route and on the pathology seriousness. Furthermore other factors are to be considered connected to the patients's age,

| | A | | B | |
|---|---|---|---|---|
| Treatment | Synovia weight (mg) | Synovia weight reduction (%) | degranulated mast cells (%) | inhibition degranulation (%) |
| Sham operated | 12.80 ± 30.3 | | 29 | |
| Physiological solution (p.s.) | 17.20 ± 1.64 | | 29 | |
| Carrageenin+ p.s. | 76.4 ± 11.59 | | 37 | |
| Carr.+ N(2-hydroxyethyl)-benzoylamide | 38.00 ± 11.59 | 50.3 | 17.2 | 53.5 | iii) Effects of N-Acyl Derivatives on Cutaneous Acute Inflammation Induced by Phorbol 12-Myristate 13 Acetate (Experimental Model for Dermal Autoimmune Pathologies).

Materials and Methods

BALB/c mice (weight 18–20 g) were housed under standard conditions (21°–23° C. in 12 h light-dark cycle with laboratory food and tap water available ad libitum).

The cutaneous acute inflammation was induced by application of phorbol-12-myristate, 13-acetate (PMA) to the ear (2. μg/ear).

Treatment

N-(2-hydroxyethyl)salicylamide was solubilized in a water:ethanol solution (20:80 v/v) to obtain the final concentration of 1% and 5%. The solution was applied 1 hour before PMA in two different administrations (−60 minutes and −30 minutes).

Results body weight and health general conditions. Anyway an acceptable therapeutic range is preferably comprised between 0.1 mg/kg and 50 mg/kg and more preferably between 0.5 and 20 mg/kg.

Relevant undesired side effects being unknown, further to a dosage, a therapeutic regimen has also to be established based on medical criteria which take into account the acuity or the chronicity characteristics of the pathology.

Typically the therapeutic regimen may have chronicity features in connection with the different pathologies, with from 1 to 2 daily administrations for at least 4 weeks. In the case of specialistic applications as for example the intraarticular, the intracerebroventricular, the retrobulbar one, weekly administration may be foreseen for at least 4 weeks.

Furthermore, as these pathologies are characterized by new acute phases of the neuroimmunogenic symptomathologies the amino-alcohol N-acyl derivatives according to the present invention can be advantageously used for a preventive action, as well as for a therapeutic one.

Under these hazard conditions these compounds can be administered as dietetic integrating components, and the daily dosage foreseen for this specific use of the compounds according to the present invention preferably range from 0.1 to 1 mg/kg, both for human beings and for animals.

The compounds according to the present invention are formulated in pharmaceutical compositions comprising all those substances suitable for the above mentioned administrations and the excipients may be those therapeutically or pharmacologically acceptable suitable for the same applications, or new excipients able to improve the vehiculation of these compounds to the site of action.

In this case also new vehicularion forms may be considered suitable, which can be obtained by bonding these compounds with specific markers of target tissues, which a preferential tropism, useful as a specific vehiculation system, exists for.

The preferred formulations for topical administration are the buffered solutions, collyria, gels, patches, lyophilized or granulated powders, suspensions, ovules, aerosols and sprays.

The topical administration of the compounds according to the present invention encompasses a dermocosmetic use in particular for preventing skin diseases having autoimmune origin. The oral systemic administration all the formulations result suitable in the form of dry powder such as granulates, tablets, dragees, perles and in the liquid form such as suspensions or oily perles.

The dietetic integrating components are preferably in the form of dragees, tablets or oily perles.

For the parenteral administration the preferred formulations are buffered aqueous solutions or oily solutions also formed by a lyophilized product readily dispersable in the solvent at the moment of the administration.

The following examples of preferred pharmaceutical compositions are reported for illustrative but not limitative purposes.

EXAMPLE 1: LACQUERED TABLETS

| Every tablet contains: | |
|---|---|
| N-palmitoylethanolamide | 30 mg |
| O.P. lactose | 80 mg |
| O.P. maize starch | 75 mg |
| O.P. talc | 5 mg |
| O.P. magnesium stearate | 2 mg |
| hydroxypropylmethylcellulose | 2 mg |
| O.P. titanium bioxide | 1.2 mg |
| yellow iron oxide (E172) | 0.2 mg |

EXAMPLE 2: JELLY PERLES

| Every perle contains | |
|---|---|
| N-palmitoylethanolamide | 100 mg |
| O.P. peanuts oil | 100 mg |
| O.P. jelly | 52 mg |
| O.P glycerin | 16 mg |
| Erythrosin (E127) | 0.1 mg |

EXAMPLE 3: LYOPHILIZED VIALS

| Every lyophilized vial contains | |
|---|---|
| N-palmitoylethanolamide | 10 mg |
| O.P. mannite | 57 mg |
| every vial contains: water for injectable formulations | 2 ml |

EXAMPLE 4: DERMATOLOGIC CREAM

| 100 g of cream contain: | |
|---|---|
| N-palmitoylethanolamide | 50 mg |
| sorbitan monostearate | 500 mg |
| polyoxyethylensorbitan monostereate | 4.5 g |
| ethyl alcohol | 3 g |
| stearic acid | 3 g |
| paraffin oil | 10 g |
| 70% sorbitol | 6 g |
| methylester of p-benzoic acid | 0.2 g |
| propylester of p-benzoic acid | 0.05 g |
| Water | q.s. to 100 g |

EXAMPLE 5: OPHTALMIC OINTMENT

| N-palmitoylethanolamide | 5 g |
|---|---|
| mineral jelly | q.s. to 100 g |

EXAMPLE 6: DIETETIC INTEGRATING COMPONENT IN JELLY PERLES

| Every perle contains: | |
|---|---|
| N-palmitoylethanolamide | 30 mg |
| egg lecithin | 90 mg |
| maize oil | 240 mg |

The pharmaceutical compositions containing as the active principles the compounds of the present invention may find a valid application in therapy of all the human and animal pathologies having autoimmune origin, characterized by mast cells hyperstimulation and wherein it is necessary to modulate the degranulation process induced by neuroimmunogenic stimuli.

The application of these compositions results particularly useful in the following human and/or animal pathologies developing at dermatologic level:

psoriasis, epidermolysis bullosa, dermatomyositis, scleroderma, pemphigus and pemphigoid; at ophtalmic level: Sjogren's syndrome, uveites and uveoretinites; at articular level, such as rheumatic arthritis, psoriatic arthritis, lupus erythematosus arthritis; at nervous level:multiple sclerosis, at the gastrointestinal level: the chronic inflammations of the gastrointestinal mucous membranes and moreover for those specific animal ophtalmologic, gastro-intestinal and articular or connective pathologies having autoimmune origin.

We claim:

1. A method for treating mammalian pathologies involving mast cell degranulation as a consequence of a neurogenic and/or an immunogenic hyperstimulation, comprising: administering an effective amount of at least an N-acyl derivative of the formula:

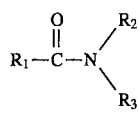

wherein $R_2$ is a residue selected from a $C_1$-$C_6$ saturated or unsaturated, linear or branched hydroxyalkyl, and $R_3$ is H or it is =$R_2$;

wherein $R_1CO$- is the acyl radical of a monocarboxylic acid belonging to one of the following classes:

a) a saturated or unsaturated, linear or branched aliphatic acid of from 2 to 20 carbon atoms;

b) a saturated or unsaturated, linear or branched aliphatic acid containing from 1 to 20 carbon atoms substituted with at least a substituent selected from the group consisting of: OH; $NH_2$; $R_4CO$-, wherein $R_4$ is a $C_1$-$C_6$ alkyl; an aryl group containing from 6 to 20 carbon atoms; a 5- or 6-membered heterocyclic group, whose ring contains at least one heteroatom selected from the group consisting of N and S; and a saturated or unsaturated 5- or 6-membered cycloalkyl optionally substituted with at least one $C_1$-$C_6$ alkyl group;

c) an aromatic acid containing from 6 to 20 carbon atoms, optionally substituted in the aromatic ring with at least one substituent selected from the group consisting of: hydroxy, $NH_2$, NH-Ph, $OCOR_4$, $OR_4$, wherein $R_4$ has the above mentioned meanings, and $SO_3H$;

d) a 5- or 6-membered aromatic heterocyclic monocarboxylic acid, whose ring contains one heteroatom selected from the group consisting of N and S, and e) a biliar acid.

2. The method according to claim 1 wherein said residues $R_3$ and/or $R_2$ are selected from the group consisting of

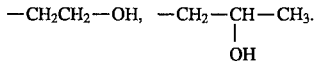

3. The method according to claim 2 wherein when $R_3$ and/or $R_2$ are

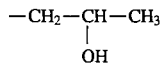

then the N-acyl derivative is optically active or it is a racemate.

4. The method according to claim 1, wherein $R_1CO$- is an acyl radical of a monocarboxylic acid belonging to class (a) selected from the group consisting of: palmitic acid, stearic acid, pentadecanoic acid, heptadecanoic acid, lauric acid, myristic acid, butyric acid, acetic acid, valetic acid, caprylic acid, valproic acid, oleic acid, linoleic acid, undecenoic acid, arachidonic acid.

5. The method according to claim 1 wherein, $R_1CO$- is an acyl radical of a monocarboxylic acid belonging to class (b), selected from the group consisting of: gamma-hydroxybutyric acid, gamma-amino-butyric acid, lactic acid, α-lipoic acid, retinoic acid, phenyl-hydroxy-acetic acid, pyruvic acid, glycolic acid.

6. The method according to claim 1 wherein $R_1CO$- is an acyl radical of a monocarboxylic acid belonging to class (c) selected from the group consisting of: salicylic, acetylsalicylic, sulfosalicylic, benzoic, p-aminobenzoic acid, trimethoxybenzoic, phenylanthranylic acid.

7. The method according to claim 1 wherein $R_1CO$ is an acyl radical of a monocarboxylic acid belonging to class (d) selected from the group consisting of: nicotinic acid, isonicotinic acid, thenoic acid.

8. The method according to claim 1 wherein $R_1CO$ is an acyl radical of a monocarboxylic acid belonging to class (e), and it is deoxycholic acid.

9. The method according to claim 1 wherein said N-acyl derivative is N-palmitoylethanolamide.

10. The method according to claim 1, wherein said N-acyl derivatives are topically administered in the form of dermocosmetic compositions for preventing skin diseases having autoimmune origin.

11. The method according to claim 1 wherein said N-acyl derivatives are orally administered in the form of dry powder pharmaceutical compositions selected from the group consisting of: granulates, tablets, dragees, perles or in a liquid pharmaceutical compositions selected from the group consisting of suspensions and oily perles.

12. The method according to claim 1 wherein said N-acyl derivatives are orally administered as dietetic integrating components, in the form of dragees, tablets or oily perles.

13. The method according to claim 12 wherein said N-acyl derivatives are administered as dietetic integrating components at daily doses ranging from 0.1 to 1 mg/kg.

14. The method according to claim 1 wherein said N-acyl derivatives are parenterally administered in the form of pharmaceutical compositions which are oily suspensions optionally formed by a lyophilized product readily dispersable in the solvent at the moment of the administration.

15. The method according to claim 1 comprising administering daily from once to twice doses ranging from 0.1 to 50 mg/kg for at least 4 weeks.

16. The method according to claim 15 wherein said doses range from 0.5 to 20 mg/kg.

17. The method according to claim 1 wherein said N-acyl derivatives are topically administered in the form of pharmaceutical compositions selected from the group consisting of: buffered solutions, collyria, gels, patches, lyophilized or granulated powders, suspensions, ovules, aerosols and sprays.

18. The method according to claim 1 wherein said mammalian pathologies are human pathologies selected from the group consisting of inflammatory demyelinating pathologies of the CNS, articular pathologies, dermal autoimmune pathologies, ophthalmic autoimmune pathologies, gastrointestinal autoimmune pathologies and connective autoimmune pathologies.

19. The method according to claim 18 wherein said connective autoimmune pathologies are selected from the group consisting of psoriatic arthritis, systemic lupus erythematosus arthritis, systemic and discoid lupus erythematosus.

20. The method according to claim 18 wherein said inflammatory demyelinating pathology of the CNS is multiple sclerosis.

21. The method according to claim 18 wherein said dermal autoimmune pathologies are psoriasis, atopic dermatitis, dermatomyositis, scleroderma, polymyositis, pemphigus, pemphigoid and epidermolysis bullosa.

22. The method according to claim 18 wherein said ophthalmic autoimmune pathologies are Sjogren's syndrome, sympathetic ophthalmia, uveitis and uveoretinites.

23. The method according to claim 18 wherein said gastrointestinal autoimmune pathologies are inflammations of the gastrointestinal mucous membranes.

24. The method according to claim 1 for preventing relapses of said mammalian pathologies involving mast cell degranulation.

25. The method according to claim 1 wherein said mammalian pathologies are animal pathologies selected from the group consisting of ophthalmic, gastrointestinal, articular and connective pathologies having autoimmune origin.

\* \* \* \* \*